US 6,488,918 B2

(12) United States Patent
Hess et al.

(10) Patent No.: US 6,488,918 B2
(45) Date of Patent: Dec. 3, 2002

(54) POWDERY COSMETIC COMPOSITION AND METHOD OF MAKING SAME

(75) Inventors: Gabriele Hess, Erzhausen (DE); Dirk Lauscher, Seeheim-Jugenheim (DE); Juergen Schmenger, Weiterstadt (DE)

(73) Assignee: Wella Aktiengesellschaft, Darmstadt (DE)

( * ) Notice: Subject to any disclaimer, the term of this patent is extended or adjusted under 35 U.S.C. 154(b) by 0 days.

(21) Appl. No.: 09/996,222

(22) Filed: Nov. 28, 2001

(65) Prior Publication Data

US 2002/0102225 A1 Aug. 1, 2002

(30) Foreign Application Priority Data

Dec. 5, 2000 (DE) .......................... 100 60 467

(51) Int. Cl.$^7$ .................. A61K 33/40; A61K 47/34; A61K 7/48; A61K 7/135
(52) U.S. Cl. .................. 424/62; 424/70.12; 424/DIG. 3
(58) Field of Search .............................. 424/62, DIG. 3, 424/70.12

(56) References Cited

U.S. PATENT DOCUMENTS

| 5,654,362 A |   | 8/1997 | Schulz, Jr. et al. ......... 524/862 |
| 5,669,916 A | * | 9/1997 | Anderson ................... 606/133 |
| 5,989,530 A |   | 11/1999 | Lorenz et al. ............... 424/62 |
| 6,074,672 A | * | 6/2000 | Dobkowski et al. ......... 424/401 |

FOREIGN PATENT DOCUMENTS

EP   0 583 767 A2   2/1994

OTHER PUBLICATIONS

International Cosmetic Ingredient Dictionary and Handbook, Ninth Edition 2002, vol. 1, p. 523.
Product Information, Personal Care Dow Corning 9506, Jun. 30, 1999.
Product Information, Personal Care, Dow Corning 9040, Aug. 23, 1999.
Patent Abstract of DE 19600225, Jul. 10, 1997.
Patent Abstract of EP 063063 B1 of Dec. 28, 1994.
Patent Abstract of DE 19853653 of May 25, 2000.

* cited by examiner

Primary Examiner—Edward J. Webman
Assistant Examiner—Helen Nguyen
(74) Attorney, Agent, or Firm—Michael J. Striker

(57) ABSTRACT

The powdery bleaching composition has improved storage stability and contains from 25 to 70 percent by weight of at least one solid per-compound as effective bleaching agent and from about 0.1 to about 20 percent by weight of at least one cross-linked silicone elastomer. The at least one cross-linked silicone elastomer is made by cross-linking with an alpha, omega-diene or a vinyl-polysiloxane and preferably is a dimethicone/vinyl-dimethicone crosspolymer or a cyclopentasiloxane and dimethicone crosspolymer. Simple methods of making the powdery cosmetic compositions are also described.

7 Claims, No Drawings

POWDERY COSMETIC COMPOSITION AND METHOD OF MAKING SAME

BACKGROUND OF THE INVENTION

1. Field of the Invention

The present invention relates to powdery cosmetic compositions and to methods of making same.

2. Description of Related Art

Conventional powdery cosmetic compositions, for example, powdery hair dye compositions, bleaching compositions and dry shampoos, are either formulated with diverse drying agents or binding agents and/or are treated by appropriate dedusting techniques.

A number of methods for making more or less dust-free powders are known in the state of the art. In these methods the dedusting of the powder usually occurs with the help of a liquid oil or wax, especially silicone oils and silicone waxes or paraffin oils and paraffin waxes. European patent application EP-OS 0 583 767 discloses a method of making a dust-free formulation, in which the powder is treated with an inert liquid, especially silicone oils or natural oils. In European Patent EP-PS 0 560 088 the dedusting of powdery bleaching agents with oils or liquid waxes, especially silicone oils or paraffin oils, is described. In German Patent Application DE-OS 19600225 the dedusting of powdery hair dye composition with oils or liquid waxes, especially silicone oils, jojoba oil or certain fatty acids and fatty alcohols, is disclosed. German Patent Application DE-OS 198 53 653 teaches a powdery composition with certain liquid solvents that are liquid at 25° C., for example hydrocarbons, alcohols, esters and ketones for dedusting. European Patent Application EP-OS 0 630 643 describes a method of making a powdery composition for dyeing and bleaching hair, in which high melting waxes are melted and then sprayed on the powder in liquid form. The previously described methods however are not optimum in every aspect, so that the powdery compositions obtained by these methods have several disadvantages, especially in regard to storage stability.

The stabilization of the powdery components during storage (i.e. during the time they are kept or preserved until they are used) is of considerable significance in the manufacture of the powdery composition in addition to its dedusting and keeping the composition dry. In order to stabilize the powder during storage, the partially very reactive powdery components of the powdery mixture must be treated so that they neither react chemically nor agglomerate.

SUMMARY OF THE INVENTION

It is an object of the present invention to provide a powdery cosmetic composition that does not have the above-described disadvantage, i.e. that has an improved storage stability.

Surprisingly it has now been found that a powdery cosmetic composition with a content of silicone elastomers does not have the above-described disadvantages.

According to the present invention a powdery cosmetic composition comprising at least one cosmetic active ingredient for treating hair and/or skin and at least one silicone elastomer has improved storage stability. The term "cosmetic active ingredient" means the principle component or components that act to perform the primary function or functions of the cosmetic composition, e.g. dye compounds in a dye composition or reducing agents in a permanent shaping composition.

The silicone elastomers, according to the invention that provide the improved storage stability, include cross-linked silicone polymers, which, for example, are obtained by cross-linking of Si—H groups (I) with an alpha, omega-diene (IIa) or a vinylpolysiloxane (IIb) in the presence of a suitable catalyst (such as a platinum catalyst) and a suitable solvent (for example, a low molecular weight linear or cyclic polysiloxane). Silicone elastomers of this type and a method for making them are described in U.S. Pat. No. 5,654,362, whose disclosure is expressly incorporated by reference herein. The acceptable range of solvents are described in this reference.

Preferably silicone elastomers with a molecular weight of more than 1000 g/mol are used in the compositions according to the invention. Especially preferred silicone elastomers include dimethicone/vinyidimethicone crosspolymer and cyclopetasiloxane and dimethicone crosspolymer, which are marketed, for example, under the respective trademarks DOW CORNING® 9506 and DOW CORNING® 9040 of Dow Corning Corp.

The cosmetic compositions of the invention preferably contain about 0.01 to about 50 percent by weight, especially about 0.1 to about 20 percent by weight, of the at least one silicone elastomer. Cosmetic compositions containing from 1 to 10 percent by weight of the silicone elastomer or elastomers are most preferred.

The powdery cosmetic composition can be, for example, a powdery hair and skin treatment composition, such as a powdery dry shampoo, or an active powder for cosmetic compositions (e.g. hair care compositions) or a powdery hair dye composition, especially a bleaching agent.

The powdery cosmetic composition can contain any and all cosmetic addition ingredients that are known or suitable for treating skin and/or hair besides or other than the silicone elastomer ingredient, for example, surfactants and emulsifiers including anionic, nonionic or ampholytic surface-active compounds, for example fatty alcohol sulfates, alkane sulfonates, olefin sulfonates, fatty alcohol polyglycol ether sulfates, alkylpolyglycosides and ethoxylated fatty alcohols, fatty acids, alkylphenols, sorbitan fatty acid esters and fatty acid alkanol amides; thickeners and gel formers, such as bentonite, fatty alcohols, fatty acids, paraffin oils, silicone oils, fatty acid esters, methyl cellulose or hydroxyethyl cellulose, starches, synthetic polymerizates, such as polyvinyl pyrrolidones and polyacrylates, or biopolymers, such as guar gum, xanthan gum, traganth, alginic acid and sodium alginate; stabilizers for peroxo compounds, such as silicates; as well as complex formers; perfiume oils, hair fixing polymers and hair care substances, such as cationic polymers, lanolin derivative compounds, jojoba oil, octyl stearate, isoparaffins, cholesterol, pantothenic acid, protein derivatives and protein hydrolyzates, provitamins and vitamins, plant extracts and inorganic or organic salts, such as aluminum, sodium, potassium and magnesium salts of higher fatty acids(e.g. stearates, palmitates, oleates, laurates, tallates or 12-hydrostearates), as well as buffer substances and agents for adjusting pH, for example organic and inorganic acids or bases, such as alkali, alkaline earth or ammonium salts.

These cosmetic ingredients are used in the powdery cosmetic composition according to the invention in an amount that is suitable for their purpose. For example, the surfactants are present in the composition according to the invention in a concentration of 0.2 to 30 percent by weight and the thickeners (not including the silicone elastomer component) are present in a concentration of from 0.1 to 25 percent by weight (in relation to the ready-to-use composition).

When the powdery cosmetic composition is a hair dye composition ("powdery dyestuff") it contains the usual oxidative dye compounds including the so-called developer substances and coupler substances and/or non-oxidative dye compounds and/or non-oxidative dyestuffs as the effective dyeing ingredient for treating hair and/or skin. The effective non-oxidative dyestuffs are selected from the group consisting of triphenylmethane dye compounds, azo dye compounds, quinone dye compounds and cationic or anionic dye compounds. These dye compounds are contained in the powdery dye composition in an amount suitable for an effective dyeing of the hair, especially in a total amount of about 0.1 to $_{25}$ percent by weight.

When the powdery cosmetic composition is a composition for de-coloring, bleaching or lightening the hair ("bleaching powder"), these powders contain a solid per-compound, such as a persulfate, percarbonate, perborate or hydrogen peroxide adduct, such as urea peroxide, as the cosmetic active ingredient for the cosmetic treatment. These per compounds are contained in the bleaching powder according to the invention in an amount that is effective for their purpose, particularly of about 25 to 70 percent by weight.

The above-described amounts relate to the total amount of the powdery cosmetic composition according to the invention.

The method of making the powdery cosmetic composition according to the invention usually comprises mixing the silicone elastomer ingredient in a suitable mixing unit with the remaining components at room temperature (about 10° to 35° C.). The silicone elastomer ingredient is dispersed, if necessary, in a natural or synthetic oil (for example liquid silicone oils or paraffin oils, plant oils, etc at 25° C.) in order to provide better distribution. The mixing unit can be any known conventional mixing apparatus, for example drum mixers, eccentric tumbling mixers, double-cone mixers, screw mixers, plough-share mixer, fluid bed mixers, telex mixers, kneading mixers or pneumatic mixers. The dispersion of the silicone elastomer ingredient in the oil preferably occurs by means of a homogenizer.

The powdery cosmetic composition according to the invention is not only completely dust-free, suitably fluid and mixable with water or aqueous preparations without any difficulty, but is very easy to make and has an outstanding strorage stability because it contains the silicone elastomer ingredient.

The subject matter of the present invention thus includes a method for making a dust-free storage stable powdery cosmetic composition by mixing the above-described silicone elastomeric ingredient with at least one cosmetic active ingredient.

The following examples illustrate the above-described invention in more detail, but the details in these examples should not be considered as limiting the claims appended hereinbelow.

EXAMPLES

Example 1

Active Powder for a Foam Care Composition (Applied with a Conventional O/W (Oil/water) Emulsion)

| | |
|---|---|
| 45.0 g | Tartaric acid |
| 50.5 g | Sodium hydrogen carbonate |
| 1.0 g | Magnesium carbonate |
| 1.5 g | Dimethicone/vinyl dimethicone crosspolymer (DOW CORNING ® 9506 of Dow Corning Corp./U.S.A.) |
| 1.0 g | Dimethicone |
| 1.0 g | Camomile powder |
| 100.0 g | |

The dimethicone/vinyldimethicone crosspolymer is first dispersed in the dimethicone. Subsequently the remaining powder ingredients are mixed with this dispersion in a mixer.

Example 2

Bleaching Powder, Dust-free (Applied with Conventional Hydrogen Peroxide Mixture)

| | |
|---|---|
| 11.6 g | Magnesium peroxide |
| 37.8 g | Ammonium peroxodisulfate |
| 11.3 g | Magnesium citrate |
| 26.3 g | Magnesium oxide |
| 3.0 g | Xanthan gum |
| 5.0 g | Dimethicone/Vinyldimethicone crosspolymer (Silicone Elastomer ® KSP-100 of Shin Etsu Silicones of America Inc./U.S.A.) |
| 5.0 g | Cyclomethicone |
| 100.0 g | |

Each individual powder component is individually treated with a sufficient amount of a dispersion of the silicone elastomer in cyclomethicone. Then the treated powder components thus obtained, which are coated with the silicone elastomer, are subsequently mixed with each other in a mixer.

Example 3

Dry Shampoo

Shampoo Powder:

| | |
|---|---|
| 75.0 g | Rice starch |
| 8.0 g | Magnesium carbonate |
| 7.0 g | Silicic acid |

-continued

| 4.0 g | Cyclopentasiloxane (and) Dimethicone crosspolymer (DOW CORNING ® 9040 of Dow Corning Corp/U.S.A.) |
| 6.0 g | Dimethicone/cyclomethicone 1:1 |
| 100.0 g | |

First the individual powder components are each individually treated with a sufficient amount of a dispersion of the cyclopentasiloxane and dimethicone crosspolymer in the dimethicone/cyclomethicone 1:1. The treated powder components obtained that are coated with the cyclopentasiloxane and dimethicone crosspolymer are subsequently mixed with each other in a mixture.

To prepare a ready-to-use dry shampoo 12.0 g of the above-described shampoo powder are packed together with 0.2 g of perfume oil, 0.5 g alpha ethylhexyl palmitate and 0.1 of sorbitan monoisostearate as well as a propellant (26.0 g propellant F152 and 61.29 dimethyl ether) in a pressurized container.

Example 4
Dust-free Bleach

| 18.0 g | Ammonium persulfate |
| 23.0 g | Sodium peroxydisulfate |
| 23.0 g | Sodium silicate, alkaline |
| 22.0 g | Magnesium carbonate |
| 2.5 g | Highly etherated methylhydroxyethyl cellulose with a viscosity of about 6000 mPas (Tylose MH 6000 YP2 of Fa. Clariant/DE) |
| 1.0 g | Ethylene diamine tetraacetate sodium salt |
| 9.0 g | Cyclomethicone |
| 1.5 g | Dimethicone/Vinyldimethicone crosspolymer (DOW CORNING ® 9506 of Dow Corning Corp/U.S.A.) |
| 100.0 g | |

A dispersion of the dimethicone/vinyidimethicone crosspolymer in the cyclomethicone is mixed with the other powder ingredients in a mixture.

Example 5
Powder Hair Dye Composition, Water Activatable (Applied with Water in a 1:4 Ratio of Powder to Water)

| 30.0 g | Sodium percarbonate |
| 20.0 g | Highly etherated sodium carboxymethyl cellulose with a viscosity of about 30000 mPas (Tylose GB 10 30000 P of Clariant/DE) |
| 4.0 g | Sodium lauryl sulfate powder |
| 10.0 g | Sodium silicate, alkali |
| 1.5 g | Ethylene diamine tetraacetate, sodium salt |
| 0.5 g | ascorbic acid |
| 13.5 g | 1,4-diaminobenzene.HCl |
| 5.0 g | 1,3-diaminobenzene.2HCl |
| 4.5 g | 2-aminophenol |
| 1.0 g | Aluminum stearate |
| 10.0 g | Cyclopentasiloxane and Dimethicone crosspolymer (Dow Corning ® 9040 of Dow Corning Corp., U.S.A.) |
| 100.0 g | |

The cyclopentasiloxane and dimethicone crosspolymer is mixed with the other powder ingredients in a mixer.

Example 6
Plant Hair Dye (Applied with Warm Water in a 1:1 to 1:2 Ratio)

| 90 g | Lawsonia Inermis |
| 2 g | Cyanopsis Tetragonalba |
| 3 g | Xanthan Gum |
| 5 g | Cyclopentasiloxane and Dimethicone crosspolymer (DOW CORNING ® 9040 of Dow Corning Corp./U.S.A.) |
| 100 g | |

The cyclopentasiloxane and dimethicone [cross polymer] crosspolymer is mixed with the remaining powder ingredients in a mixture.

Example 7
Plant Hair Dye, Natural Blond (Applied with Warm Water in a Ratio of 1:1 to 1:2)

| 40 g | Cassia Auriculata |
| 25 g | Acacia Catechu |
| 17 g | Lawsonia Inermis |
| 6 g | Selvia Officinalis |
| 2 g | Cyanopsis Tetragonalba |
| 3 g | Xanthan gum |
| 7 g | Cyclopentasiloxane and Dimethicone crosspolymer, (DOW CORNING ® 9040 of Dow Corning Corp. U.S.A.) |
| 100 g | |

The cyclopentasiloxane and dimethicone crosspolymer is added slowly with stirring portion-wise to the remaining powder ingredients in a mixer.

Example 8
Powder Hair Dye Composition, Water Activatable (Applied with Water in a 1:4 Ratio of Powder to Water)

| 0.33 g | 2,5-diaminotoluene sulfate |
| 0.33 g | 2,5-diaminophenylethanol sulfate |
| 0.22 g | N,N-bis-(β-hydroxyethyl)-p-phenylenediamine sulfate |
| 0.33 g | 4-amino-3-methylphenol |
| 0.22 g | 2-aminomethyl-p-aminophenol.HCl |
| 0.22 g | 4,5-diamino-1-hydroxyethyl pyrazole sulfate |
| 0.22 g | 4,5-diamino-1-(p-methylbenzyl)-pyrazole sulfate |
| 0.11 g | 1-naphthol |
| 0.11 g | 3,4-diaminobenzoic acid |
| 0.11 g | 1-(β-hydroxyethylamino)-3,4-methylenedioxybenzene.HCl |
| 0.11 g | 2,4-diamino-1-(β-hydroxyethoxy)benzene sulfate |
| 0.11 g | 5-amino-6-chloro-2-methylphenol |
| 0.11 g | 1,3-bis-2,4-(diaminophenoxy)propane.2HCl |
| 0.11 g | 3-aminophenol |
| 0.11 g | 4-chlororesorcinol |
| 0.11 g | 5-amino-2-methylphenol |
| 0.11 g | 2-amino-4-(β-hydroxyethylamino)anisole sulfate |
| 0.11 g | 2,4-diamino-1-fluoro-5-methylbenzene sulfate (1:1) |
| 0.11 g | 3,5-diamino-2,6-dimethoxypyridine.2HCl |
| 0.11 g | resorcinol |
| 0.11 g | 2-methyl resorcinol |
| 0.11 g | m-dimethylaminophenylurea |
| 0.02 g | 2-amino-5-methylphenol |
| 0.02 g | 2-amino-6-chloro-4-nitrophenol |
| 0.02 g | 4-(β-hydroxyethylamino)-3-nitrophenol |
| 0.02 g | 4-[3-hydroxypropyiamino]-3-nitrophenol |
| 0.02 g | N-(2-hydroxyethyl)-2-nitro-p-phenylenediamine |
| 0.02 g | 4-amino-3-nitrophenol |
| 0.02 g | 2-amino-4,6-dinitrophenol |
| 0.02 g | 2-hydroxyethylpicramic acid |
| 0.02 g | 1-N-hydroxyethylamino-4-methyl-2-nitrobenzene |
| 0.02 g | 6-ethylamino-2-chloro-4-nitrophenol |

-continued

| | |
|---|---|
| 0.02 g | 2,6-diamino-3-((pyridin-3-yl)azo)pyridine |
| 0.02 g | 4-nitrophenylaminoethylurea |
| 30.00 g | Percarbonate |
| 20.00 g | Highly etherated sodium carboxymethyl cellulose with a viscosity of about 30000 mPas (Tylose GB 30000P of Clariant, DE) |
| 0.08 g | NaOH |
| 0.33 g | Ethylene diamine tetracetate |
| 0.33 g | $Na_2SO_3$ |
| 1.5 g | Dimethicone/Vinyldimethicone crosspolymer |

(DOW CORNING ® 9506 of Dow Corning Corp./U.S.A.)

The cyclopentasiloxane and dimethicone crosspolymer is added slowly with stirring portion-wise to the remaining powder ingredients in a mixer.

The disclosure in German Patent Application 100 60 467.6 of Dec. 6, 2000 is incorporated here by reference. This German Patent Application describes the invention described hereinabove and claimed in the claims appended hereinbelow and provides the basis for a claim of priority for the instant invention under 35 U.S.C. 119.

While the invention has been illustrated and described as embodied in a powdery cosmetic composition and method of making same, it is not intended to be limited to the details shown, since various modifications and changes may be made without departing in any way from the spirit of the present invention.

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention.

What is claimed is new and is set forth in the following appended claims.

We claim:

1. A powdery bleaching composition comprising
   from 25 to 70 percent by weight of at least one solid per-compound as effective bleaching agent; and
   from about 0.01 to 50 percent by weight of at least one silicone elastomer;
   wherein said at least one silicone elastomer is selected from the group consisting of dimethicone/vinyldimethicone crosspolymer and cyclopentasiloxane and dimethicone crosspolymer.

2. The powdery bleaching composition as defined in claim 1, wherein said at least one silicone elastomer consists of said dimethicone/vinyldimethicone crosspolymer.

3. The powdery bleaching composition as defined in claim 1 or 2, further comprising at least one of dimethicone and cyclomethicone.

4. The powdery bleaching composition as defined in claim 1, further comprising from 0.2 to 30 percent by weight of at least one surfactant selected from the group consisting of anionic surface-active compounds, nonionic surface-active compounds and ampholytic surface-active compounds.

5. The powdery bleaching composition as defined in claim 1, further comprising from 0.1 to 25 percent by weight of at least one thickener.

6. The powder bleaching composition as defined in claim 1, further comprising at least,one salt selected from the group consisting of alkali salts, alkaline earth salts and ammonium salts.

7. A powdery bleaching composition comprising
   from 25 to 70 percent by weight of at least one solid per-compound as effective bleaching agent; and
   from about 0.1 to about 20 percent by weight of at least one cross-linked silicone elastomer;
   wherein said at least one cross-linked silicone elastomer is made by crosslinking at least one silicone elastomer with a vinylpolysiloxane or an alpha, omega-diene in the presence of a catalyst and in a linear or cyclic polysiloxane solvent.

* * * * *